United States Patent [19]

Alban

[11] Patent Number: 4,505,278

[45] Date of Patent: Mar. 19, 1985

[54] PAIN THRESHOLD GAGE AND SOFTNESS TESTER

[76] Inventor: Eugene P. Alban, 1267 S. Beach St., Daytona Beach, Fla. 32014

[21] Appl. No.: 485,952

[22] Filed: Apr. 18, 1983

[51] Int. Cl.³ ............................................. A61B 10/00
[52] U.S. Cl. .................................. 128/774; 128/645; 73/81
[58] Field of Search ........................ 128/744, 774, 645; 73/78, 81, 83, 88

[56] References Cited

U.S. PATENT DOCUMENTS

| | | | |
|---|---|---|---|
| 2,119,699 | 6/1938 | Bloom | 73/81 |
| 2,421,449 | 6/1947 | Zuber | 73/81 |
| 2,453,841 | 11/1948 | Gluzek | 128/744 |
| 2,822,544 | 9/1950 | Seyboth | 73/81 X |
| 3,628,526 | 12/1971 | Bigliano | 128/645 X |
| 4,159,640 | 7/1979 | Leveque et al. | 128/774 X |
| 4,365,638 | 12/1982 | Leveque et al. | 128/774 |

*Primary Examiner*—Edward M. Coven
*Attorney, Agent, or Firm*—Warrick E. Lee, Jr.

[57] ABSTRACT

A device for determining a patient's threshold of pain having a gas-tight member, such as a cylinder, for confining a fixed amount of gas and a two-ended member, such as a rod. A first end of the rod is pressed against the patient's body to apply gradually increasing pressure, and a second end decreases the volume of the fixed amount of gas. Indicia are provided for indicating how much the volume of gas decreases. The device may also be modified to test materials for softness or firmness.

6 Claims, 7 Drawing Figures

PAIN THRESHOLD GAGE AND SOFTNESS TESTER

This invention relates to a device for measuring the amount of pressure a part of the body can withstand before feeling pain. Such devices are useful to physicians in detecting parts of the body having illness or injury and in determining the extent of the illness or injury. This invention also provides a gage for measuring the degree of softness or hardness of a patients flesh or other material.

Prior art pain threshold gages consist of a spring loaded plunger connected to a dial indicator. When the physician presses the plunger against the patient's body, the dial reading is proportional to the amount of pressure applied. The physician gradually increases the pressure until the patient experiences pain. Since dial indicators are expensive, these prior-art devices are expensive. Other prior-art devices use springs and rods to measure the amount of pressure applied. See for example U.S. Pat. No. 1,637,421. However, this type of device still contains at least one metal spring which can be an expensive item.

Other prior-art devices, not directed to pain threshold, use various types of springs. See for example U.S. Pat. No. 2,704,539 wherein there is disclosed a skin sensitivity detector having a metal spring with a spring-tension-adjusting device. U.S. Pat. No. 3,933,148 discloses a device for scraping across the skin at fixed pressure to determing the amount of streaking such scraping causes on the skin. The fixed pressure may be provided by spring systems, such as, elastic springs, gas springs, hydraulic springs, and pneumatic springs. However, neither of these patents is concerned with applying gradually increasing pressure to the patients body to determine pain threshold.

The present invention provides a very inexpensive pain threshold gage that requires no expensive metal springs or a dial indicator. The device has a very high degree of accuracy at low pressures, where high accuracy is desired. Preferred embodiments also provide a means for measuring the degree of softness or firmness of a patient's flesh or other materials. Such measurements are also highly desirable to physicians and other users.

The present invention comprises apparatus for applying gradually increasing pressure against the body of a patient to determine pain threshold comprising:

(a) gas-tight means for confining a fixed amount of gas, (b) two-ended means having first end for pressing against the patient's body to apply pressure and a second end adapted to decrease the volume of the fixed amount of gas when said first end is pressed against the patient's body, and (c) indicia for indicating the decrease in volume of the fixed amount of gas.

DETAILED DESCRIPTION OF THE INVENTION

Figure 1:
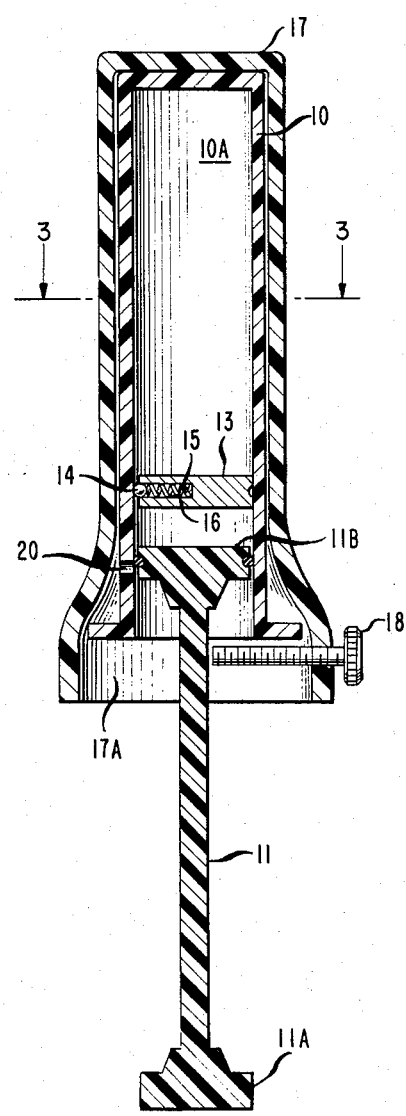
FIG. 1 is a longitudinal sectional view of a preferred embodiment of a pain threshold gage in accordance with the invention.

Referring to FIG. 1, there is shown apparatus for applying gradually increasing pressure against a patient's body to determine pain threshold. Gas-tight means for confining a fixed amount of gas, such as air, are provided. Such means are preferably in the form of a hollow cylinder 10, having cylindrical bore 10A. A two-ended means is provided having a first end for applying pressure to the patients body and a second end adapted to decrease the volume of the fixed amount of gas. In FIG. 1 two-ended rod 11 has first end 11A, which is a tip having fixed area. Rod 11 has second end 11B which is a piston that slides within the bore 10A of cylinder 10. Piston 11B fits tightly, but slidingly against bore 10A, providing a movable gas-tight seal. Hence as end 11A is pressed against a patient's body with gradually increasing force, piston 11B gradually slides upward within cylinder 10, decreasing the volume, but not the amount of the gas trapped in bore 10A.

Figure 2:
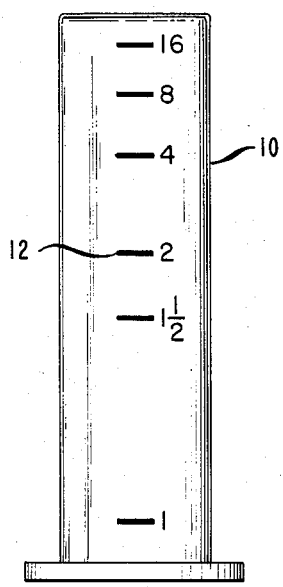
FIG. 2 is a view of the outside of cylinder 10 of FIG. 1.

Indicia are provided to indicate the decrease in volume caused by piston 11B's movement upward within cylinder 10. Preferably cylinder 10 is sufficiently transparent so that the position of piston 11B is visable through the walls of cylinder 10. Indicia 12 may then be printed or etched on the wall of cylinder 10, as shown in FIG. 2.

In order to temporarily preserve a reading of how far piston 11B had traveled within bore 10A, it is highly preferable to provide a loose-fitting plug 13 within cylinder bore 10A. Plug 13 has a small ball 14 that is pushed against the wall of cylinder 10 by spring 16, located in slot 15. Hence plug 13 may travel easily within bore 10A when pushed ahead of piston 11B. However, when piston 11B withdraws, plug 13 is held in its position of furthest travel by ball 14 and spring 16.

A transparent cover 17 may enclose cylinder 10. Cover 17 has an opening 17A for rod 11. Bolt 18 is provided to hold piston 11B and cylinder 10 within cover 17.

A small hole 20 is located at the base of cylinder 10 for equalizing gas pressure in the cylinder with atmospheric pressure.

Figure 3:
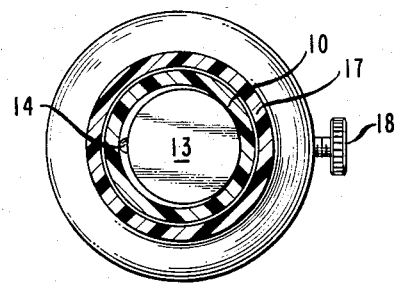
FIG. 3 is a sectional view of FIG. 1 taken along section 3—3.

It is preferred that cover 17, cylinder 10 and plug 13 have circular longitudinal cross sections as shown in FIG. 3. However, any cross-section having a bore of uniform shape in which a similarly shaped piston may slide is acceptable. Hence the term "cylinder" as used in the claims is not to be retricted to cylinders having circular cross sections.

The apparatus of FIG. 1 functions as follows. First the operator, such as a physician, withdraws rod 11 as far out of cylinder 10 as bolt 18 will allow, thereby placing bore 10A in fluid communication with atmospheric pressure via hole 20 and correcting for any variations in atmospheric pressure since the last use of the device. The operator then presses tip 11A against the body of the patient at the point where injury is suspected. The operator applies gradually increasing pressure until the patient expresses pain. As the pressure against the body is gradually increased, rod 11 pushes piston 11B upward within bore 10A, compressing and increasing the pressure of the fixed amount of air confined there. Piston 11B pushes plug 13 ahead of it. As soon as the patient expresses pain, the operator withdraws the device, causing the compressed air to push piston 11B and rod 11 downward. However plug 13 remains in place, giving the operator a reading of the amount of pressure that was applied when the patient expressed pain.

To reset plug 13 to the base of cylinder 10, the operator merely shakes the device in the same manner that a thermometer is "shaken down", to move plug 13 downward by centrifugal force.

The device of FIG. 1 may be constructed very inexpensively. Cylinder 10 may be made on transparent plastic or glass on machinery normally used to manufacture barrels for hypodermic syringes. Member 11 may be very similar to a plunger rod for a hypodermic syringe. Since the pressure applied by the operator is inversely proportional to the volume of gas in the cylinder, indicia 12 are preferably an inverse scale as shown in FIG. 2. The device may be calibrated theoretically based on the ideal gas laws, or by pressing the device against a scale. Once calibration for one device is established, duplicate devices will have the same calibration and can therefore use the same indicia.

Figure 4:
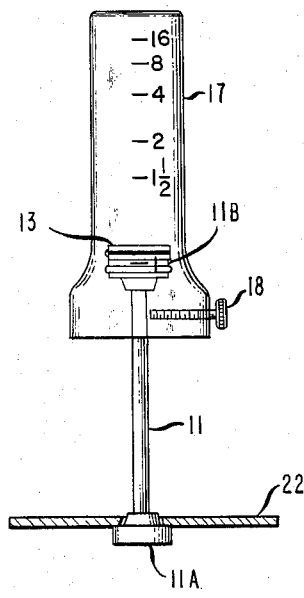
FIG. 4 shows apparatus in accordance with the invention adapted to measure skin firmness or softness.
Figure 5:
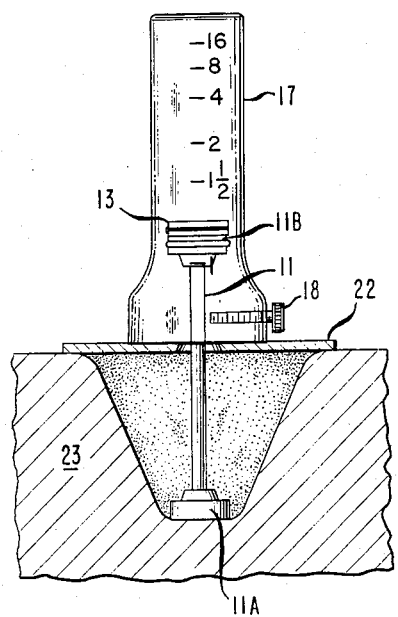
FIG. 5 shows the apparatus of FIG. 4 applied against soft flesh or other material.
Figure 6:
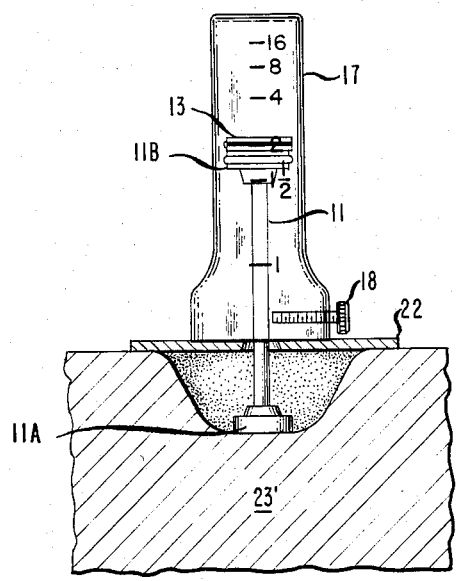
FIG. 6 shows the apparatus of FIG. 4 applied against material having a medium degree of softness.
Figure 7:
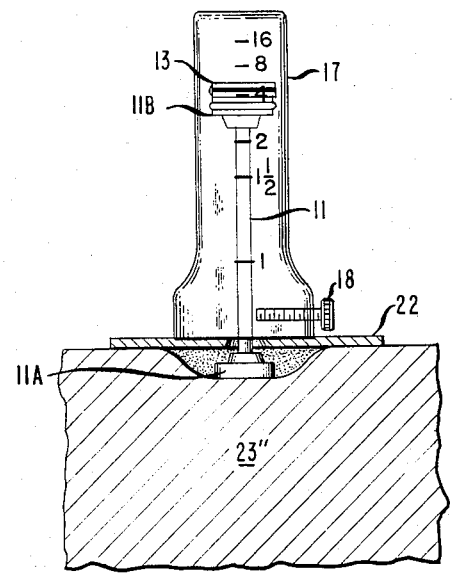
FIG. 7 shows the apparatus of FIG. 4 applied against hard material.

FIG. 4 illustrates a device similar to that of FIGS. 1, 2, and 3, but having a flat plate 22 slidably mounted on rod 11 between ends 11A and 11B outside of the cylinder. Plate 22 enables the operator to test a patient's flesh for softness, which is useful information to physicians. Other materials, such as mattresses and cushions may also be tested for softness with the device. The embodiment of FIG. 4 operates as follows. The operator presses end 11A against the patient's flesh 23 to be tested for softness until plate 22 contacts the base of cover 17 as shown in FIGS. 5, 6, and 7. If the flesh is very soft, the internal pressure reading of the device will be low when plate 22 contacts cover 17, as shown in FIG. 5. FIG. 6 shows how an intermediate internal pressure reading occurs if the flesh has medium firmness. On hard flesh, a high internal pressure reading is reached before plate 22 contacts cover 17, as shown in FIG. 7.

What is claimed is:

1. Apparatus for measuring the softness of materials comprising:
   (a) a hollow gas-tight cylinder for confining a fixed amount of gas, said cylinder having a transparent wall,
   (b) a two-ended rod having a first end for pressing against the material and a second end being a piston adapted to slide in said cylinder to decrease the volume of the fixed amount of gas when said first end is pressed against the material,
   (c) indicia on the transparent wall of said cylinder for indicating the decrease in volume of the fixed amount of gas, and
   (d) a plate slidably mounted on said rod between said first and second ends outside of said cylinder, whereby said plate slides along said rod when said first end is pressed against the material and eventually contacts said cylinder to provide an indication of softness.

2. Apparatus for applying gradually increasing pressure against the body of a patient to determine pain threshold comprising:
   (a) a hollow gas-tight cylinder for confining a fixed amount of gas, said cylinder having a transparent wall,
   (b) a two-ended rod having a first end for pressing against the patient's body to apply pressure and a second end being a piston adapted to slide in said cylinder to decrease the volume of the fixed amount of gas when said first end is pressed against the patient's body, and
   (c) indicia on the transparent wall of said cylinder for indicating the decrease in volume of the fixed amount of gas.

3. The apparatus of claim 2 further comprising a loose-fitting plug located within said cylinder ahead of said piston and means for preventing said plug from freely sliding within said cylinder, whereby said plug is pushed by said piston to the maximum amount of travel by said piston, but remains in the position of maximum travel when the apparatus is withdrawn from the patient's body.

4. The apparatus of claim 3 further comprising a plate slidably mounted on said rod between said first and second ends outside of said cylinder, whereby said plate slides along said rod as pressure is applied to the patient's body and eventually contacts said cylinder to provide an indication of softness.

5. The apparatus of claim 2 wherein said cylinder has an opening in its wall near its base for equalizing gas pressure in the cylinder with atmospheric pressure and further comprising:
   a transparennt cover enclosing said cylinder and means for holding said piston and cylinder within said cover.

6. The apparatus of claim 5 further comprising a plate slidably mounted on said rod between said first and second ends outside of said cylinder, whereby said plate slides along said rod as pressure is applied to the patient's body and eventually contacts said cover to provide an indication of softness.

* * * * *